US008793869B2

(12) United States Patent
Dye et al.

(10) Patent No.: US 8,793,869 B2
(45) Date of Patent: *Aug. 5, 2014

(54) METHOD FOR PRODUCING A MULTIELECTRODE LEAD

(75) Inventors: Don Dye, Plano, TX (US); John W Swanson, Lake Oswego, OR (US); Jerome J Boogaard, Forest Grove, OR (US); Dave Locke, Vancouver, WA (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 618 days.

This patent is subject to a terminal disclaimer.

(21) Appl. No.: 13/070,181

(22) Filed: Mar. 23, 2011

(65) Prior Publication Data

US 2011/0167631 A1    Jul. 14, 2011

Related U.S. Application Data

(63) Continuation of application No. 12/763,021, filed on Apr. 19, 2010, now Pat. No. 7,934,366, which is a continuation of application No. 11/869,844, filed on Oct. 10, 2007, now Pat. No. 7,698,883, which is a continuation of application No. 11/285,826, filed on Nov. 22, 2005, now Pat. No. 7,287,366.

(60) Provisional application No. 60/630,323, filed on Nov. 23, 2004.

(51) Int. Cl.
*H01B 7/04* (2006.01)
*B65H 81/08* (2006.01)

(52) U.S. Cl.
USPC .................. 29/857; 29/868; 29/749

(58) Field of Classification Search
USPC .......... 29/857, 868, 869, 872, 749, 755; 52/6, 52/10, 17, 18
See application file for complete search history.

(56) References Cited

U.S. PATENT DOCUMENTS

| | | | |
|---|---|---|---|
| 3,736,739 A | 6/1973 | Walter | |
| 3,934,395 A | 1/1976 | Vryland | |
| 4,484,586 A | 11/1984 | McMickle et al. | |
| 5,142,100 A * | 8/1992 | Vaupotic | 29/857 X |
| 5,979,288 A | 11/1999 | Gallagher et al. | |
| 6,125,532 A * | 10/2000 | Takada | 29/749 X |
| 6,952,616 B2 | 10/2005 | Wessman et al. | |
| 7,239,922 B1 | 7/2007 | Boogaard et al. | |
| 7,287,366 B2 | 10/2007 | Dye et al. | |
| 7,698,883 B2 | 4/2010 | Dye et al. | |
| 2010/0193065 A1 | 8/2010 | Dye et al. | |

FOREIGN PATENT DOCUMENTS

EP    455212 A2 * 11/1991

* cited by examiner

*Primary Examiner* — A. Dexter Tugbang

(57) ABSTRACT

Fabricating an implantable stimulation lead by advancing work material to be wrapped with wire conductors, then, operating a plurality of payout carriers to let out the wire conductors, rotating the plurality of payout carriers to wrap the wire conductors about the work material, providing an amount of twist to each wire conductor as the wire conductors are let out, forming a lead body using the wrapped conductors, and fabricating a plurality terminals on the lead body, wherein the plurality of terminals are electrically connected to the conductive wires.

21 Claims, 11 Drawing Sheets

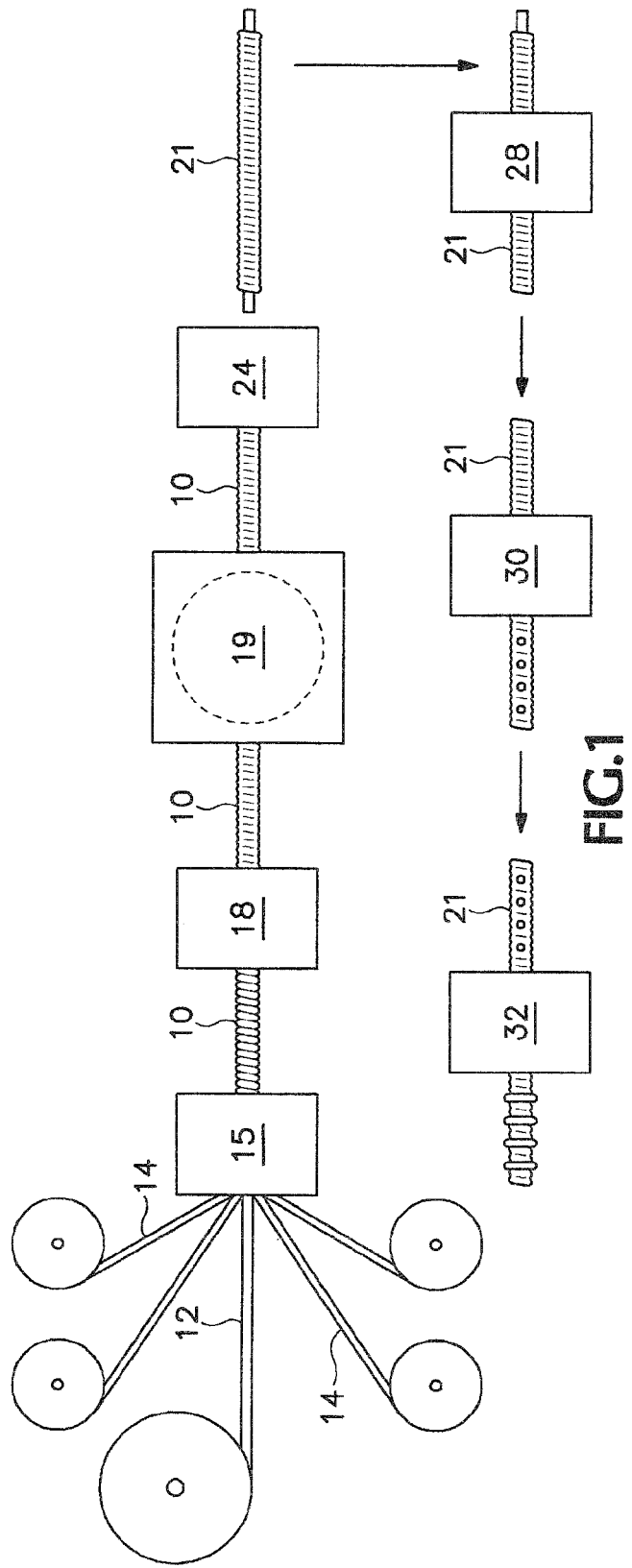
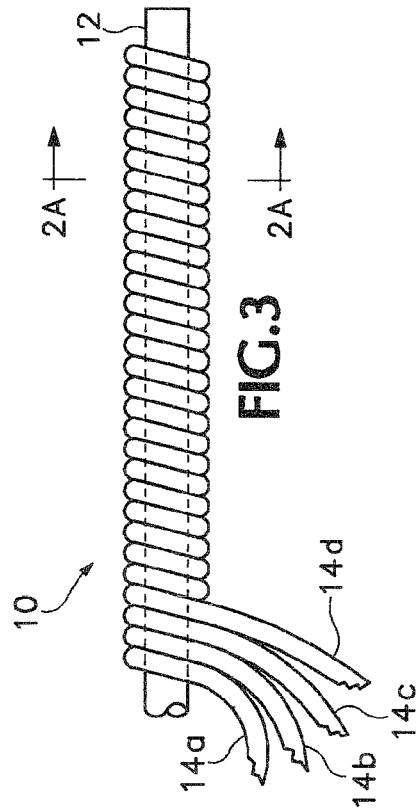
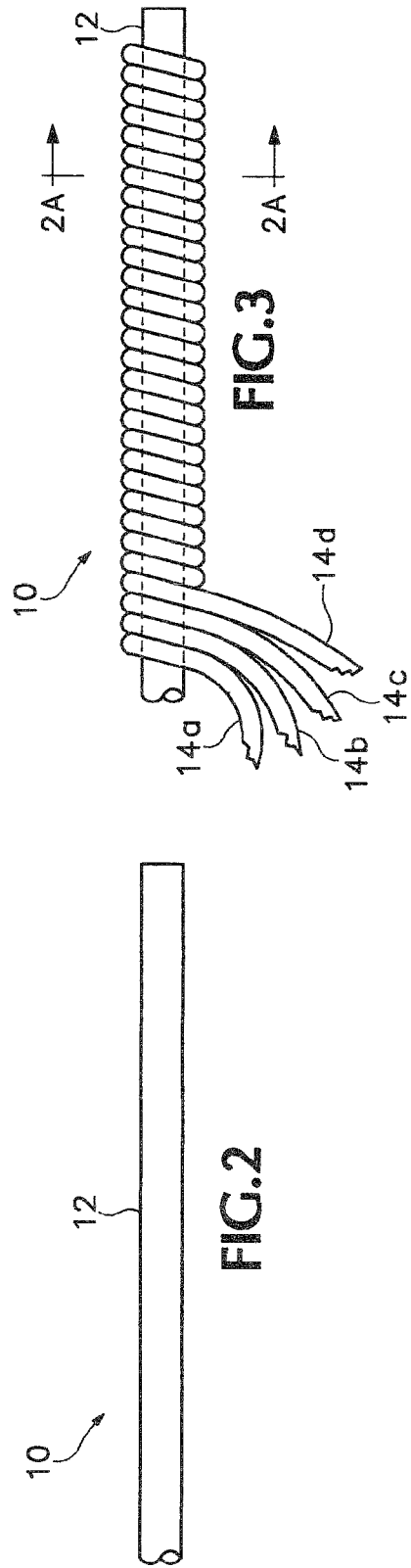

METHOD FOR PRODUCING A MULTIELECTRODE LEAD

CROSS-REFERENCE TO RELATED APPLICATIONS

This application is a continuation of U.S. application Ser. No. 12/763,021, filed Apr. 19, 2010, pending, which was a continuation of U.S. application Ser. No. 11/869,844, filed Oct. 10, 2007, now U.S. Pat. No. 7,698,883, which was a continuation of U.S. application Ser. No. 11/285,826, filed Nov. 22, 2005, now U.S. Pat. No. 7,287,366, which claims the benefit of U.S. Provisional Application No. 60/630,323, filed Nov. 23, 2004, the disclosure of which is incorporated herein by reference.

BACKGROUND

Bioelectrical stimulus leads in general and pain management leads in particular have proven to be an important addition to mankind's set of tools for addressing bodily malfunction. Unfortunately, heretofore these leads have been made one at a time in a fairly expensive operation that included the use of a lathe to turn a set of insulated wires together about a mandrel and then the application of heat and pressure to fuse the insulation of the wires together. Additionally, at least in part because the lathe wrapping process results in a lead body having a varying outer diameter and insulation thickness, the previous method has encountered a fairly high defect rate, driving up the price for correctly manufactured leads. Later operations, in which electrodes are created in the lead body require a uniform outer diameter and insulation thickness to avoid frequent accidental damage to the lead bodies, due to an uncertain amount of insulation removal needed to reach the underlying wire. This uncertainty has made it impractical to automate the process.

A separate problem that occurs when helically winding wires about a mandrel is that of residual stress being imparted to the wires. In the prior art, two basic options are available for this kind of wire wrapping. In both options, a set of payout carriers are mounted on a turn table having a central aperture through which the core being wrapped is advanced. The turntable is rotated about this mandrel and the payout carriers let out wire, which helically wraps the mandrel. In a first option, known as a planetary system, the payout carriers are maintained in a stationary orientation relative to an absolute coordinate system. In the second option, the payout carriers are maintained in a stationary orientation relative to the turntable ("stationary re turntable" case). For each option, however, residual stress is imparted to wires as they are wrapped because the ideal amount of payout carrier rotation falls in between the planetary case and the stationary re turntable case.

Also, some references show a lead being made by taking a group of insulated wires and binding them together with an additional application of curable insulation. Although this is a workable method, the step of applying an additional coat of insulation requires some time for the insulated wires to be dipped into the curable insulating material, and then requires some time for that material to be cured. It would be advantageous to find some other way of binding a set of insulated wires together.

BRIEF SUMMARY

In a first separate aspect, the present invention is a method of producing a plurality of multi-electrode leads that uses a set of insulated wires. These wires are continuously stranded together, thereby forming a stranded portion. Then the wires of the stranded portion are continuously fused together, thereby creating a fused portion.

In a second separate aspect, the present invention is a length of working material, more than two meters (six feet) long, comprising a flexible central mandrel and insulated wires helically wrapped about the central mandrel and fused together.

In a third separate aspect, the present invention is a production facility for producing multi-electrode leads. The facility includes a wire wrapping device adapted and configured to wrap a mandrel with insulated wires and a radiant energy application device, located so as to continuously receive the wrapped mandrel, the radiant energy application device being adapted to apply radiant energy to the wrapped mandrel, sufficient to fuse the insulated wires together.

In a first separate aspect, the present invention is a helically wrapped wire device wherein a set, of wires are arranged helically about a core region and wherein each wire defines a central axis and wherein each wire goes through less than 0.1 rotations about its central axis for every complete rotation about the core region.

In a second separate aspect, the present invention is a wire wrapping device that includes a turntable assembly that is made up of a turntable and a driver adapted to rotate the turntable. Also, a set of payout carriers are mounted on the turntable, each payout carrier adapted to let out wire to be wrapped. A driver is adapted to turn each payout carrier relative to the turn table, the driver being user adjustable to turn each payout carrier by a selectable amount, per each complete rotation of the turntable.

In a third separate aspect, the present invention is a method of wrapping a central mandrel with flexible longitudinal elements. In the method a set of payout carriers are revolved about the central mandrel as the central mandrel is moved along its length and the payout carriers payout the flexible longitudinal elements, thereby helically wrapping the mandrel with the flexible longitudinal elements. Also, the payout carriers are rotated a user-selected amount per rotation of the turntable.

In a first separate aspect, the present invention is a method of making a multi-electrode probe, that starts with a length of a working material comprising a set of insulated wires arranged so that they are touching along their lengths. The working material is moved continuously in a lengthwise manner through a radiant energy application zone, where radiant energy is applied to the working material, thereby heating the working material to soften a portion of the insulation and render it adhesive. The softened insulation is permitted to adhere together and re-cool, thereby fusing together the insulated wires.

In a second separate aspect, the present invention is a reflow assembly, comprising a radiant energy application device, adapted to create plural radiant energy application zones, the plural radiant energy application zones being longitudinally and angularly displaced from each other. In addition, a movement assembly is adapted to move a continuous length of working material through the radiant energy application zones.

In a first separate aspect, the present invention is a helically wrapped wire device wherein a set of wires, insulated from one another and each having a wire central axis, are arranged helically about a core region defining a device central axis, and wherein at each point along each wire a radial distance may be defined between the wire central axis and the device central axis, and wherein the radial distances, over the entirety of the device do not vary by more than 100 microns.

In a second separate aspect, the present invention is a method of producing a multi-electrode probe, starting with a wrapped wire work piece having a set of wires, each surrounded by insulation which is fused together into a unitary mass and each having a most radially outward surface, which is radially outward relative to the work piece, the work piece defining a work piece central axis, and wherein at each point along each wire a radial distance may be defined between the work piece central axis and the most radially outward surface of the wire. Also, at least one prospective electrode point is defined along the most radially outward surface of each wire, each prospective electrode point having an actual radial distance that is within 100 micrometers of an ideal predetermined radial distance for the prospective electrode point. An energy beam is used to create an aperture through the insulation at each prospective electrode point, the application of the energy beam being facilitated by the actual radial distance being within 100 micrometers of the ideal radial distance.

In a first separate aspect, the present invention is a wire wrap device, comprising a turntable and a set of payout carrier assemblies positioned on the turntable. Each payout carrier includes, a spool bearing wire, an electric motor operatively connected to the spool; and an electric motor control assembly adapted to control the electric motor to maintain a selected tension on the wire.

In a second separate aspect, the present invention is a method of wrapping a central mandrel with flexible longitudinal elements. The method includes revolving a set of payout carriers about the central mandrel as the central mandrel is slowly moved along its length and the payout carriers payout the flexible longitudinal elements, thereby helically wrapping the mandrel with the flexible longitudinal elements. In addition, each payout carrier has a spool that is turned by an electric motor and also has a longitudinal element tension measurement device. The tension is regulated by controlling the electric motor in response to the tension measurement device.

In a first separate aspect, the present invention is a wire wrap device, comprising a turntable assembly that, in turn, includes a turntable that defines a central aperture, and payout carriers mounted on the turntable. In addition a payout assembly is adapted to payout flexible mandrel and a flexible mandrel guide assembly is adapted to guide the flexible mandrel through the aperture and to maintain the flexible mandrel in a constant rotational orientation.

In a second separate aspect, the present invention is a helically wrapped wire work piece, comprising a mandrel and a set of insulated wires, wrapped about the mandrel. The mandrel is not twisted anywhere over its length at a twist rate of more than one complete rotation per one meter of mandrel.

The foregoing and other objectives, features and advantages of the invention will be more readily understood upon consideration of the following detailed description of the preferred embodiment(s), taken in conjunction with the accompanying drawings.

BRIEF DESCRIPTION OF THE DRAWINGS

FIG. 1 is a block diagram of a preferred manufacturing process according to the present invention.

FIG. 2 is a side view of a continuous work piece at a first stage in the process of FIG. 1.

FIG. 3 is a side view of the work piece of FIG. 2 at a later stage in the process of FIG. 1.

DETAILED DESCRIPTION

Referring to FIGS. 1 through 8, the following text describes a preferred method of the present invention in schematic overview. A more detailed discussion of the critical steps follows.

Figures 4A, 4B, 4C:
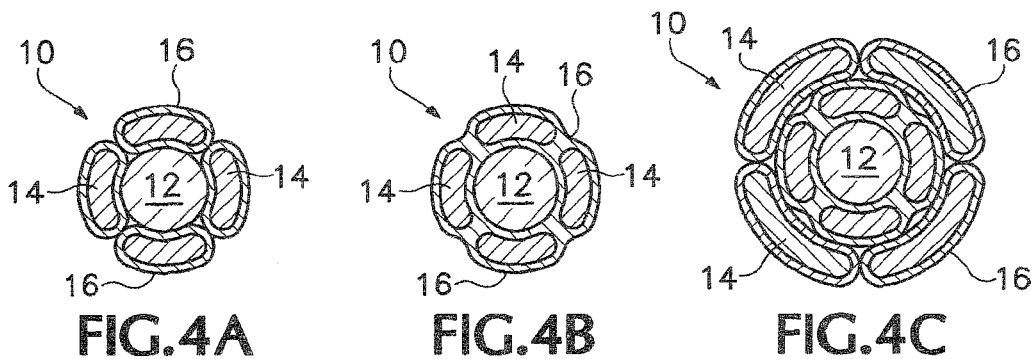
FIG. 4A is a cross-sectional view of the working material of FIG. 3.
FIG. 4B is a cross-sectional view of the working material of FIG. 7.
FIG. 4C is a cross-sectional view of a working material according to an alternative embodiment, including a second layer of wires.

A preferred method for practicing the present invention begins with a continuous working material 10, which at the process beginning is only a poly tetrafluoroethylene coated stainless steel mandrel wire 12. The working material 10 is then helically wrapped with a set of four insulated wires 14a, 14b, 14c and 14d (collectively 14) at a wire wrapper 15. Each of the wires 14 includes a layer of insulation 16. While four insulated wires are used in one embodiment, those skilled in the art will recognize that any suitable number of wires may be wrapped onto mandrel 12, using the methods of the present invention. The use of four wires in particular is not intended to be part of the invention. Referring to FIG. 4c, in one embodiment, one or more additional layers of wires are wound in helices over the initial layer of wires 14. Typically, each additional layer of wires would be wound in the opposite direction to the layer immediately below.

Figure 5:
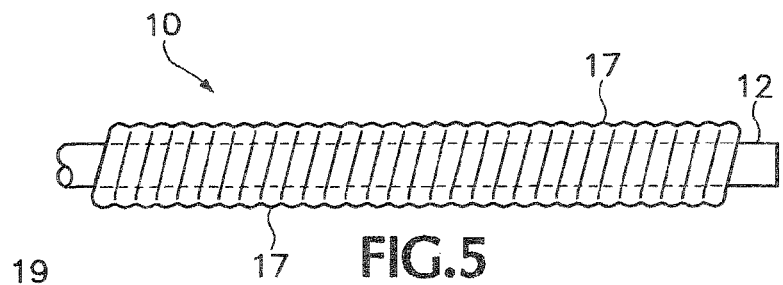
FIG. 5 is a side view of the work piece of FIG. 3 at a first sub-stage of a further stage in the process of FIG. 1.

Working material 10, now comprising mandrel 12 and helically wrapped insulated wires 14 (FIG. 4) may now be spooled and later unspooled (not shown) or fed directly to the next step in the process. In this next step, working material 10 may be selectively and repeatedly heated in a multistage reflow oven 18 (FIG. 1). The wires 14 are heated to a temperature that causes the insulation 16 of insulated wires 14 to approach or achieve a phase change, thereby becoming soft and adherent and ultimately fusing together, by heating, melting and re-solidifying, in a set of angular regions 17 (FIG. 5). This process is preferably repeated, by feeding working material 10 through additional stages of reflow oven 18, until the insulation 16 is fused together over its entire angular extent.

In an alternative embodiment, the insulation of each wire 16 is chosen so that its phase transition temperature, $T_g$, is different from the $T_g$ of the insulation 16 of the neighboring wires 14. In particular, one or more wires 14 may have insulation 16 having a $T_g$ that is high enough so that it does not undergo a phase change in the reflow oven 18, and emerges intact to lend desired physical characteristics (such as enhanced stiffness) to the working material 10. In another alternative preferred embodiment (not shown), spacers may be used to impart desired physical characteristics, such as stiffness, to the overall working material 10.

Figure 6:
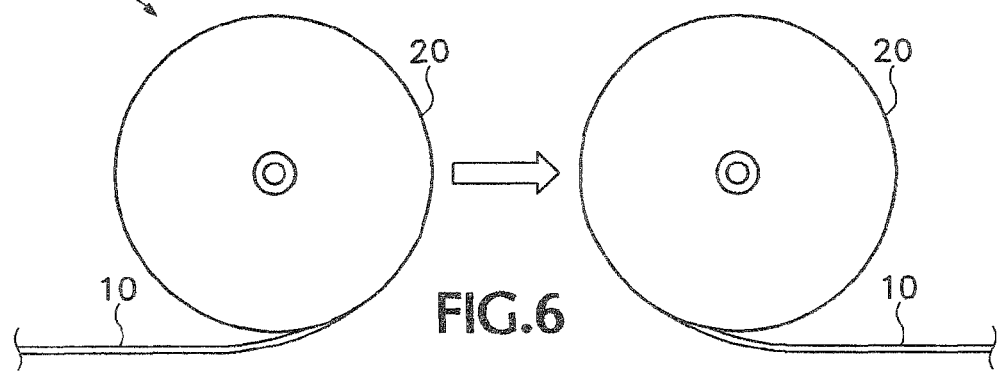
FIG. 6 is an illustration of an optional step in the process of FIG. 1.
Figure 7:
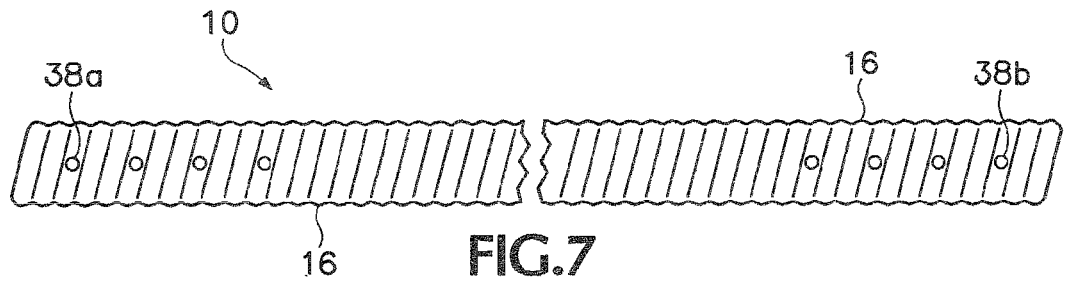
FIG. 7 is a side view of an individual work piece in a further stage of the process of FIG. 1.
Figure 8:
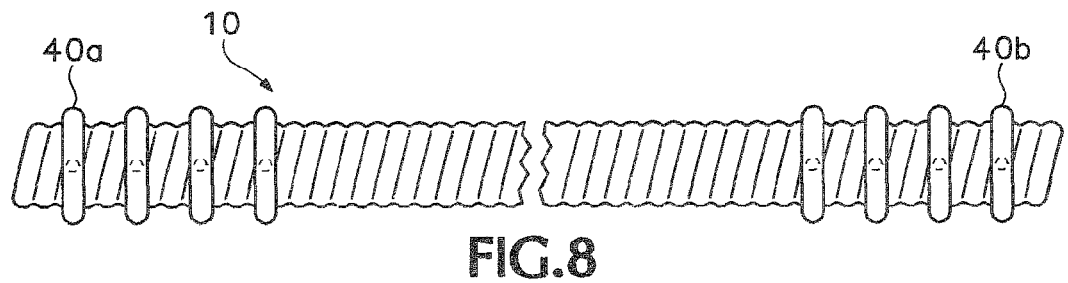
FIG. 8 is a side view of a finished product of the process of FIG. 1.

At this point, the working material 10, now comprising mandrel 12 having insulated wires 14 at least partially fused about it, may now be spooled onto a spool 20 and stored for later work (optional step 19 in FIG. 1, shown in FIG. 6). Alternatively, step 19 is not performed and working material 10 proceeds directly to the remaining steps. Continuous working material 10 is cut (step 24) into individual lead bodies 21. Each individual lead body 21 may have a length of from about 10 cm (4 in) to about 150 cm (60 in).

After the lead bodies 21 have been cut to length, mandrel 12 must be removed from within in a mandrel removal step 28. This task may be facilitated by a coating of mandrel 12 that will ease removal, such as a PTFE coating. The mandrel removal step 28 may be a simple hand operation by a human worker.

Next, in an electrode creation step 30 a proximal aperture 38a (FIG. 7) and a distal aperture 38b are created through insulation 16 for each one of wires 14. This task is performed by a laser machining station, preferably equipped with four (4) nd:YAG frequency multiplied lasers or other ultraviolet light lasers. Other removal steps may be used such as that disclosed in U.S. Pat. No. 6,952,616 is incorporated by reference as if fully set forth herein.

In a ring attachment step 32, a power source ring connector 40a is attached at each proximal aperture 38a and a tissue stimulating ring electrode 40b is attached at each distal aperture 38b. This may be done by constructing a column of conductive material and laser welding ring 40a or 40b to this column. One preferred method of attaching ring electrodes is described in patent application Ser. No. 10/700,110 filed on Nov. 3, 2003, which is assigned to the same assignee as the current application and is incorporated by reference as if fully set forth herein.

In one preferred embodiment mandrel 12 has an outer diameter of 330 microns (13 mils) and insulated wires 14 each have a diameter of 273 microns (10.75 mils), which after some compression results in an individual lead bodies 21 having an diameter of about 711 microns (28 mils).

Throughout the process as described above and in greater detail below, great care is taken to create a lead body 21 having uniform insulation thickness. It is in the creation of the apertures 38a and 38b through insulation 16 that this effort bears fruit, because it is far easier, and less prone to error, to laser machine a lead body having a uniform outer diameter (and therefore uniform laser range) then a non-uniform lead body. Particularly troubling is the case in which the range is too close, and too much insulation is removed, potentially ruining the entire end product.

Figure 9:
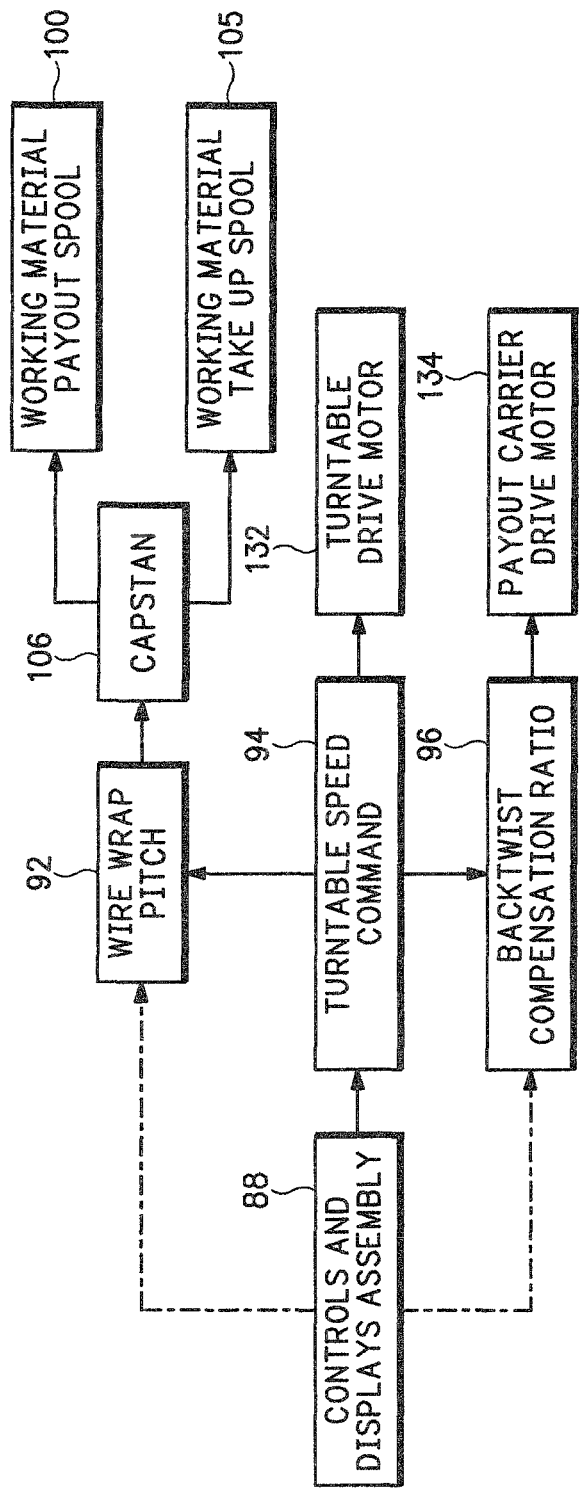
FIG. 9 is a block diagram of a wire wrap process that forms a portion of the process illustrated in FIG. 1.
Figure 10:
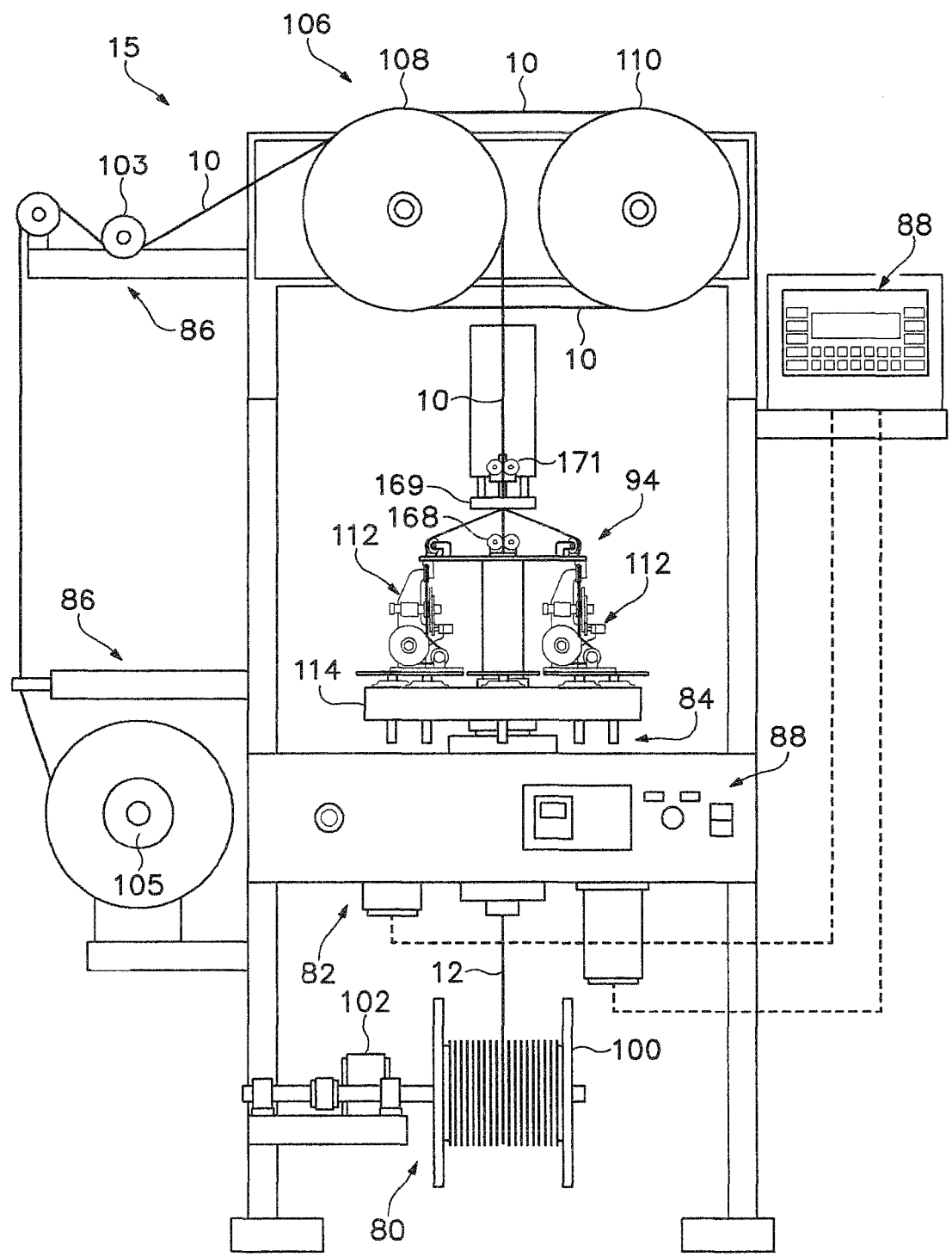
FIG. 10 is a front view of a wire wrapping device according to the present invention.

FIGS. 9 and 10-15 describe the wire wrap process and the wire wrapper 15 used for helically wrapping the mandrel or core in greater detail. Referring to FIG. 10 for a high level depiction of the wire wrapper 15, the wire wrap process begins with a mandrel payout assembly 80 and a working material take up assembly 86 that together maintain working material 10 in well regulated motion and tension along its path. Simultaneously a controls and displays assembly 88 controls a power and linkage assembly 82, which powers a wire payout assembly 84. Although one preferred embodiment permits the use of a keyboard for user input of control parameters, as indicated in FIG. 10, an alternative embodiment provides a simple set of manual controls, such as knobs, for controls and display assembly 82.

Assembly 84 includes a turntable 114 upon which a set of payout carriers 112 are supported. Wire wrapper 15 is configured to permit a variable degree of back twist compensation, which is implemented by rotating carriers 112 relative to turntable 114 at an operator specified rate. In one embodiment an operator manipulates controls and displays assembly 88 to place the right amount of back twist compensation onto wires 14. In an alternative embodiment, the operator enters the wire and mandrel dimensions and the pitch at which the wires are to be wrapped and assembly 88 computes the degree of back twist compensation necessary to prevent residual stress being placed onto wires 14.

Avoiding the placement of residual stress on wires 14 is necessary so that this stress does not cause the wires to move spontaneously later in the process, causing a deformation in the final shape of the lead body 10, or inconsistent wire locations. After wrapping is complete, wrapped mandrel is spooled by working material take up assembly 86, which maintains a constant tension to avoid deforming the working material 10. In an alternative preferred embodiment, working material 10 is not spooled but progresses immediately to the next stage of processing.

In greater detail, the progress of working material 10 is maintained by the payout assembly 80 and the take up assembly 86. The payout assembly 80 includes a mandrel payout spool 100, a payout motor 102 and a dancer arm tension measurement device (not shown). Motor 102 is responsive solely to the tension measurement, thereby maintaining constant tension on working material 10. In take up assembly 86, working material take up spool 105 is also motor driven (not shown) and solely responsive to tension measurement arm 103. Take up spool 105 is moved cyclically into and out of the plane of FIG. 10, thereby causing working material 10 to spool in a repeated pattern. The tension placed on working material 10 can be changed by changing the weighting on either dancer arm 103 or the payout assembly 80 dancer arm (not shown).

An additional portion of take up assembly 86 is the capstan 106, which includes an equal-diameter pair of wheels 108 and 110, about which working material 10 is looped several times. Each wheel 108 and 110 bears several grooves along its exterior rim, to permit this looping while preventing the working material 10 from ever rubbing against itself. Capstan 106 is driven by an electric motor (not shown) and serves the function of stabilizing working material 10 as it exits wrapping guide plate 169 (FIG. 11).

Figure 11:
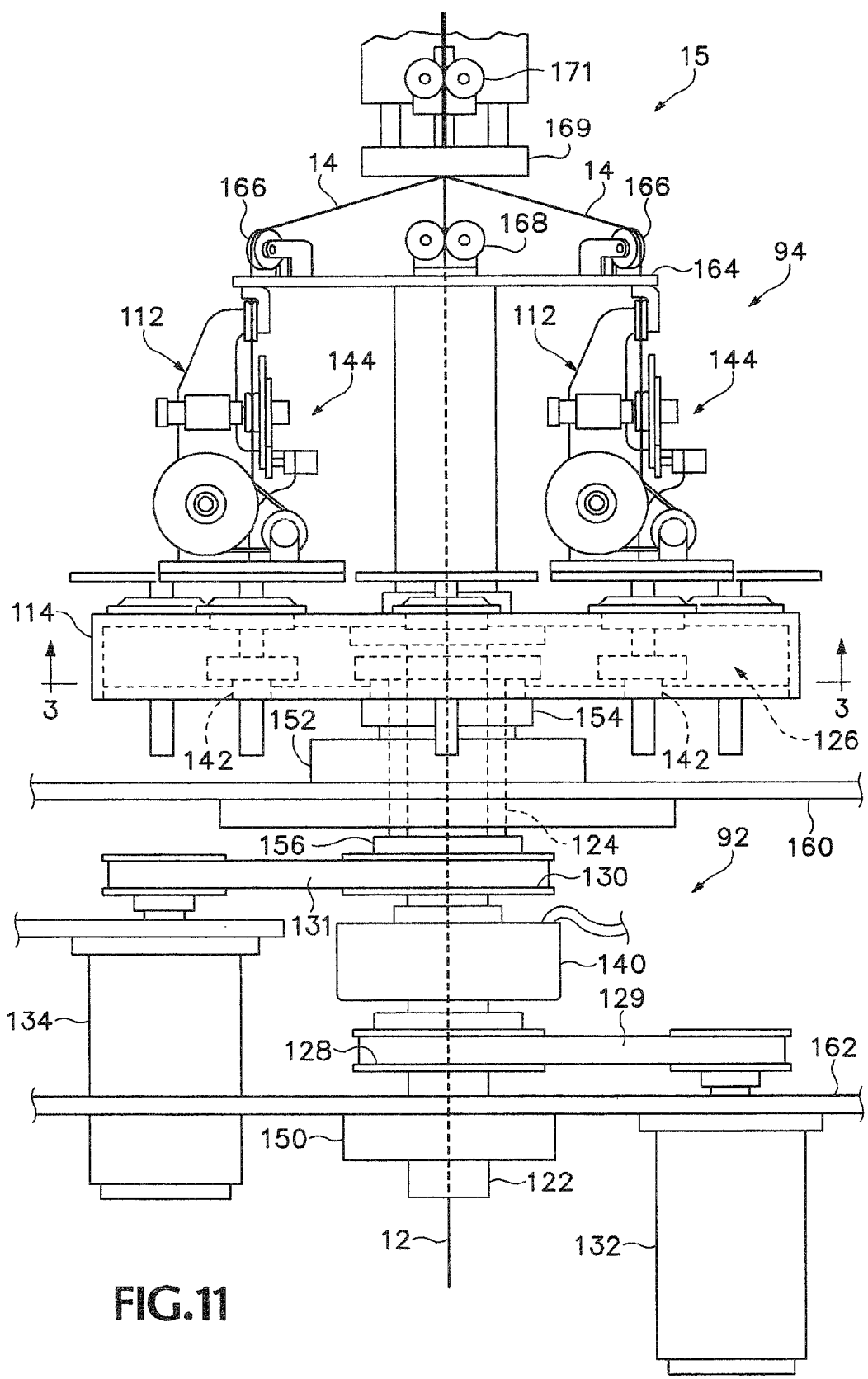
FIG. 11 is a partial front of the wire wrapping device of FIG. 10, showing some features obscured from view by the front panel shown in FIG. 9.

Referring to FIG. 9, for a more complete description of the control scheme of wrapper 15, the wire wrap pitch 92, which in practice is the ratio between the capstan 106 rotation rate and the turntable 114 rotation rate 96 (which equals the rotation rate of a turntable drive motor 132 [FIG. 11]) may be set prior to beginning a wire wrapping run. Likewise the back-twist compensation ratio 96, which is the ratio of a payout carrier drive motor 134 rate [FIG. 11] to the turntable drive motor 132 rate, may be set at the same time. Then, during a run, the speed of the entire process may be changed by changing the turntable rotation rate command 94, which changes the capstan 106 turn rate and payout carrier drive motor 134 rate, automatically. In other words, during operation, the capstan 106 drive and the payout carrier drive motor 134 are slaved to the turntable drive motor 132. The rate of capstan 106 effectively controls the turn rate of take up spool 105 (FIG. 10) and pay out spool 100 (FIG. 10) as both these spools are controlled to place a fixed tension on working material 10, and this can only be accomplished if they turn at the same average rate as capstan 106.

Referring to FIG. 11, power and linkage assembly 82 (FIG. 10) includes an inner shaft 122 which drives the turntable 114, and an outer shaft 124 which drives the payout carriers 112, by way of a system of gears 126. Inner shaft and outer shaft are driven by a first pulley 128 and a second pulley 130, respectively. Each of these pulleys 128, 130 are driven by a belt 129 and 131, respectively, that is in turn driven by the turntable motor 132 and the payout carrier motor 134, respectively.

The two motors 132 and 134 are managed by the control assembly 88 (FIG. 10), which regulates their relative speed within a range of relative speeds. As noted previously, the turn rate ratio of these two motors is set before a production run is begun. In one preferred embodiment this range extends from equal speed (payout carriers 112 stationary relative to the turntable 114) to the case where the outer shaft rotates at one half the speed of the inner shaft (payout carriers 112 stationary relative to an absolute frame of reference).

Figure 13:
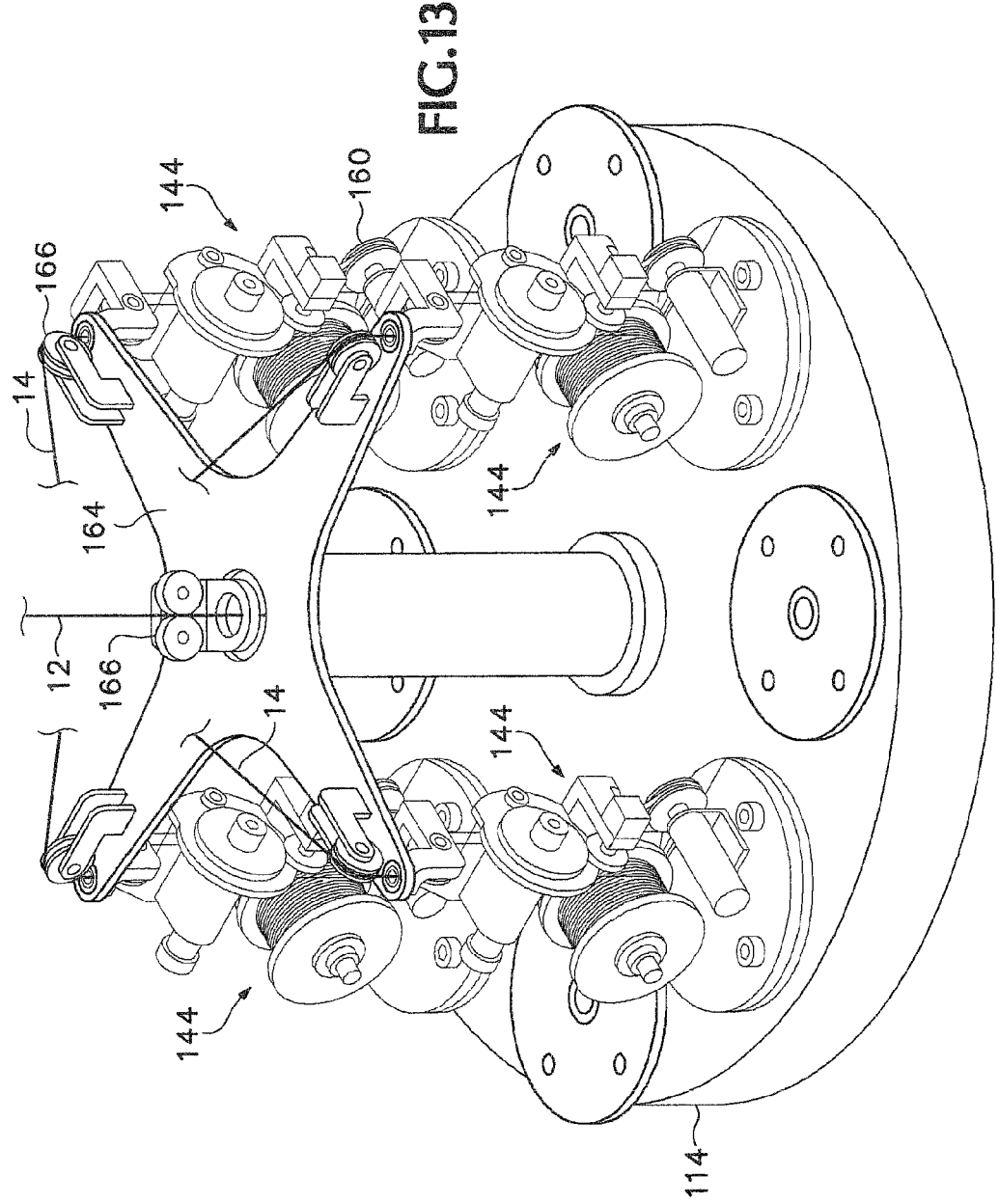
FIG. 13 is a perspective view of a portion of the wire wrapping device of FIG. 10, showing the payout carrier turntable.

A number of features shown in FIGS. 11 and 13 facilitate the workings of the embodiment. A slip ring 140 permits electric power to be transmitted to the rotating inner assembly that includes shafts 122 and 124. On turn table 114, each payout carrier 112 includes a slip ring 142 near its base for supplying electricity to the payout carrier 112. Each payout carrier 112 includes an electric wire tension control assembly 144 that maintains a constant tension on the insulated wire 14 that is being threaded onto working material 10. Bearing assemblies 150, 152, 154 and 156 facilitate the rotation of shafts 122 and 124. Plates 160 and 162 support power and linkage assembly 82. A spider 164 supports a wire guide wheel 166 for each payout carrier 112, to further restrain the wires 14 as turntable 114 rotates. A first pair of pinch wheels 168 acts as an anti-rotation device for mandrel 12, to prevent it from being twisted by the torque imparted by wires 14, as they are being wrapped. In addition, a guide plate 169 defines an aperture that helps stabilize mandrel 12 and wires 14 at the point that the actual wrapping takes place. Finally, a second pair of pinch wheels 171 act to further stabilize the mandrel 12. Together pinch wheel pairs 168 and 171 form a guide path for and prevent rotation of mandrel 12.

Figure 12:
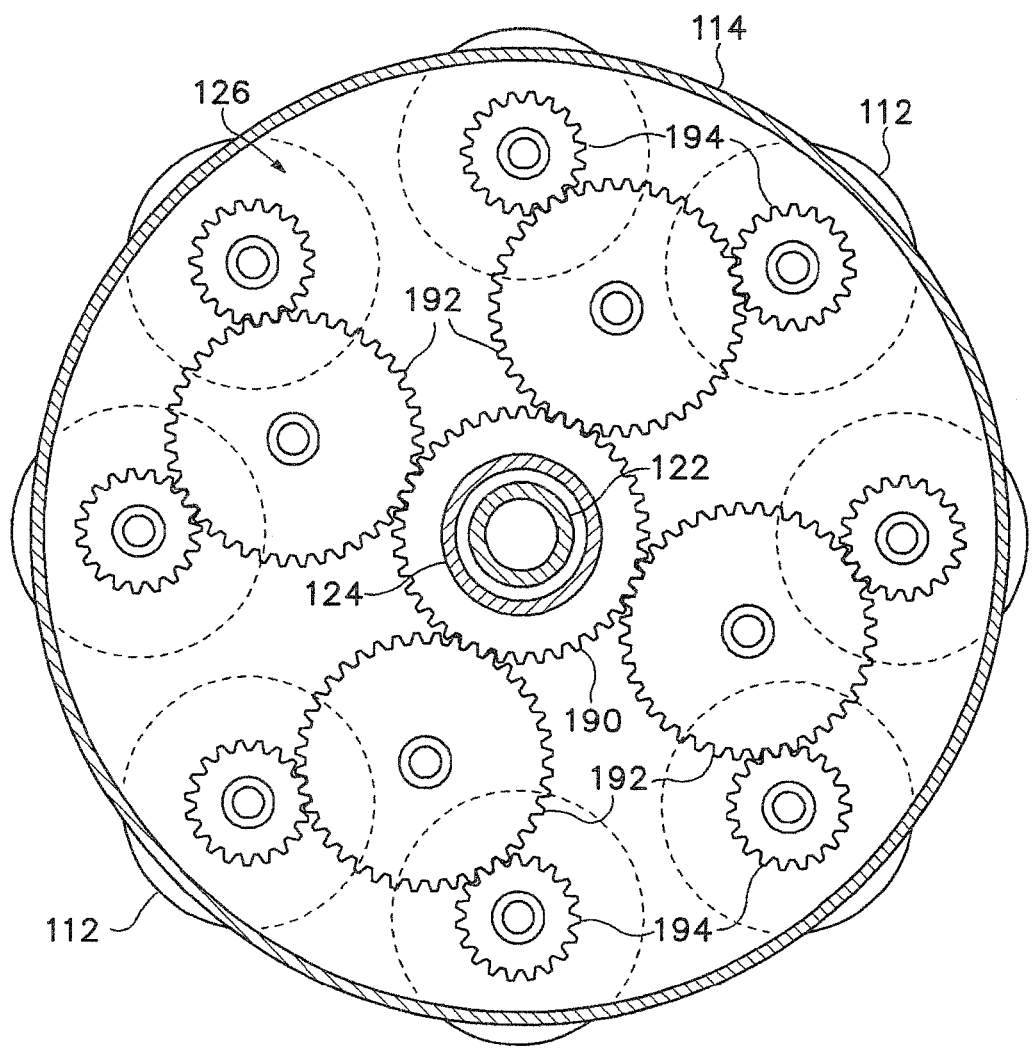
FIG. 12 is a partial top view of the wire, wrapping device of FIG. 10, showing the payout carrier gears.
Figure 14:
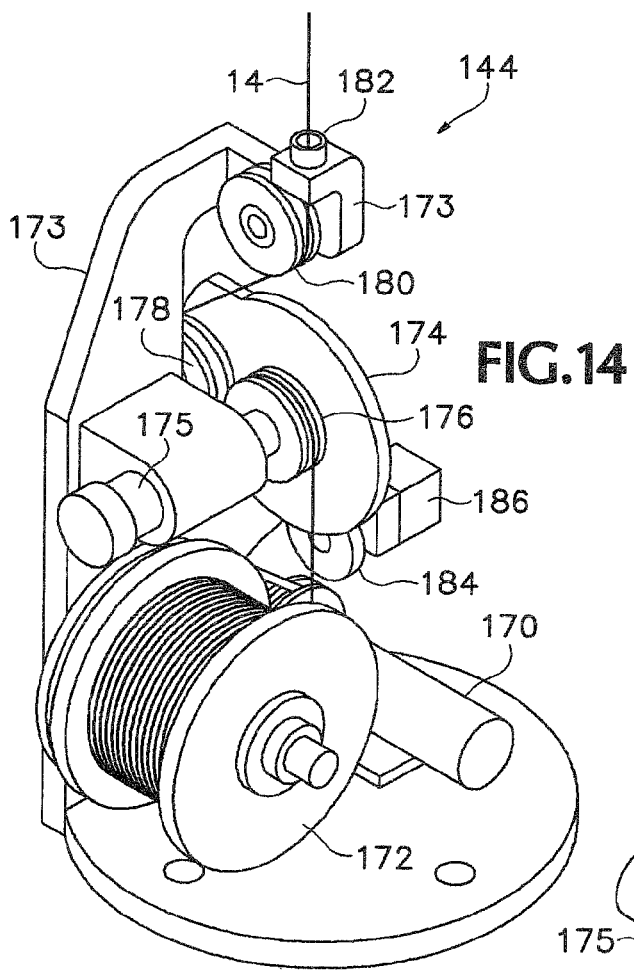
FIG. 14 is a perspective view of a single one of the payout carriers of the wire wrap device of FIG. 10.
Figure 15:
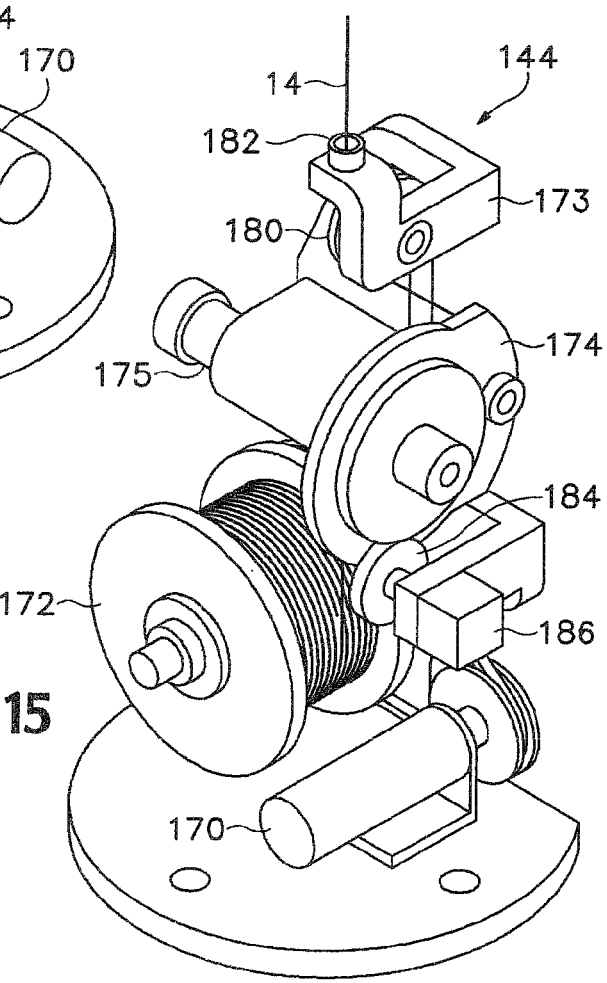
FIG. 15 is an alternative perspective view of a single one of the payout carriers of the wire wrap device of FIG. 10.

Referring to FIGS. 12, 14 and 15, each electric wire tension control assembly 144 includes an electric motor 170 that drives a spool 172, both of which are mounted on a payout carrier frame 173. A wire 14 follows a path defined by a dancer arm 174 which is rotatably mounted by way of an axle 175 to frame 173. Dancer arm 174 has a first dancer arm guide wheel 176 and a second dancer arm guide wheel 178 about which wire 14 is threaded in an "S-pattern." Wire 14 proceeds about a frame guide wheel 180 and through a payout carrier exit guide 182. A dancer arm position measurement unit 184 monitors the position of arm 174 and sends this information to an electric motor controller 186. Controller 186 commands the rate at which electric motor 170 turns. This arrangement permits control of the tension in wire 14 to an accuracy of about +1%.

Referring to FIG. 12, a system of gears 126 links the motion of outer shaft 124 with that of the payout carriers 112. An outer shaft gear 190, rigidly attached to outer shaft 124, causes a set of intermediate gears 192 to counter rotate. Each gear 192 causes a pair of payout carrier gears 194 to rotate in the same direction as gear 190. The size of gears 192 is chosen simply to permit each gear 192 to mesh with two gears 194. The number of teeth of gear 192 is transparent to the turning ratios of gears 190 and 194. Gears 194 have half the number of teeth of gear 190, so that a half counter rotation of gear 190, relative to turntable 114, causes each gear 194 to go through a complete counter rotation relative to turntable 114. Accordingly, if the outer shaft is turning at half the speed of the inner shaft, each payout carrier 112 undergoes a complete counter rotation per rotation of turntable 114, thereby remaining stationary relative to a fixed frame of reference. If outer shaft 124 turns at the same rate as inner shaft 122, there is no relative rotation between any of the gears 190, 192 and 194, which causes the payout carriers 112 to remain stationary relative to the turn table 114.

Figure 16:
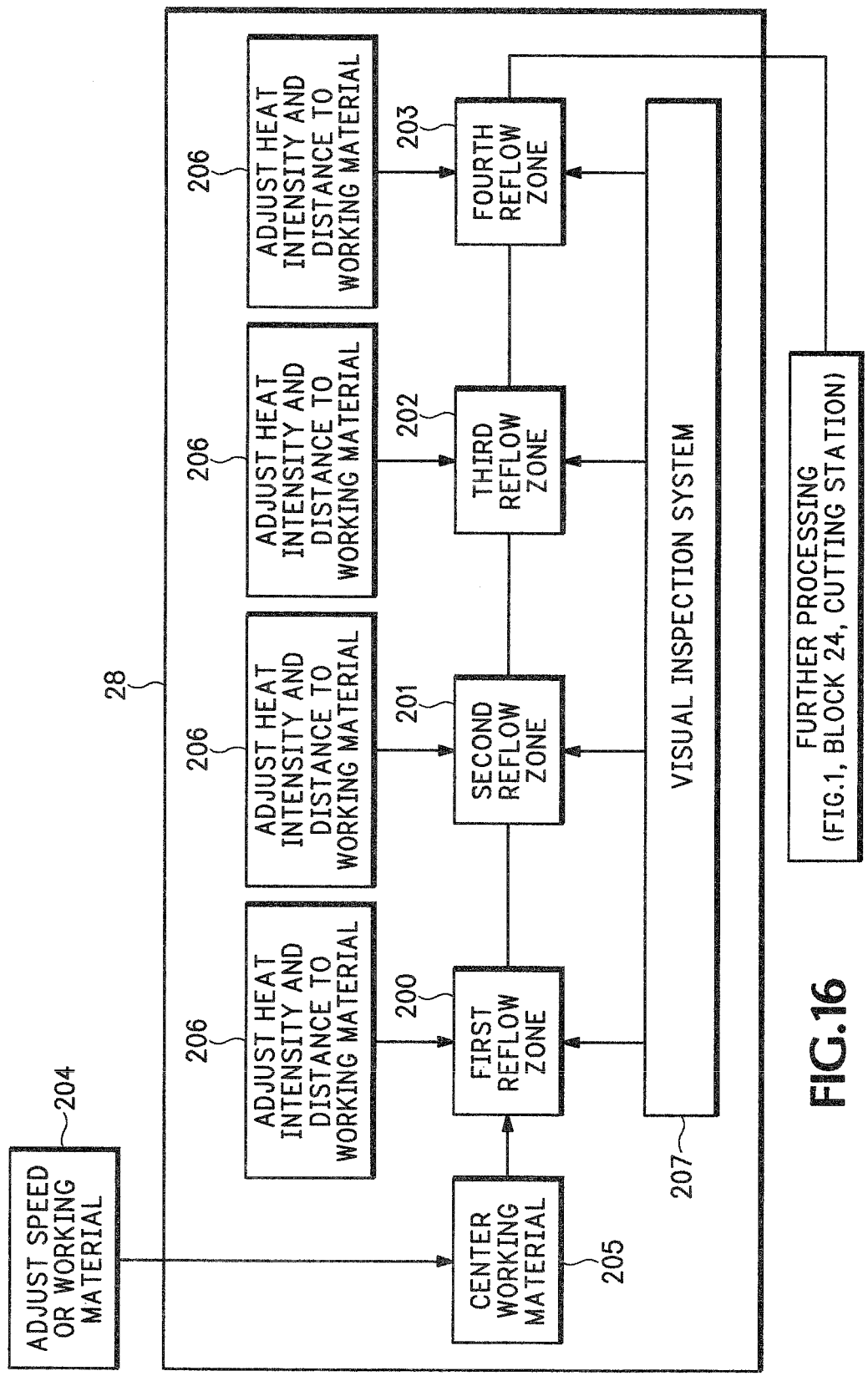
FIG. 16 is a block diagram of the insulation fusing portion of the lead production process of FIG. 1.
Figure 17:
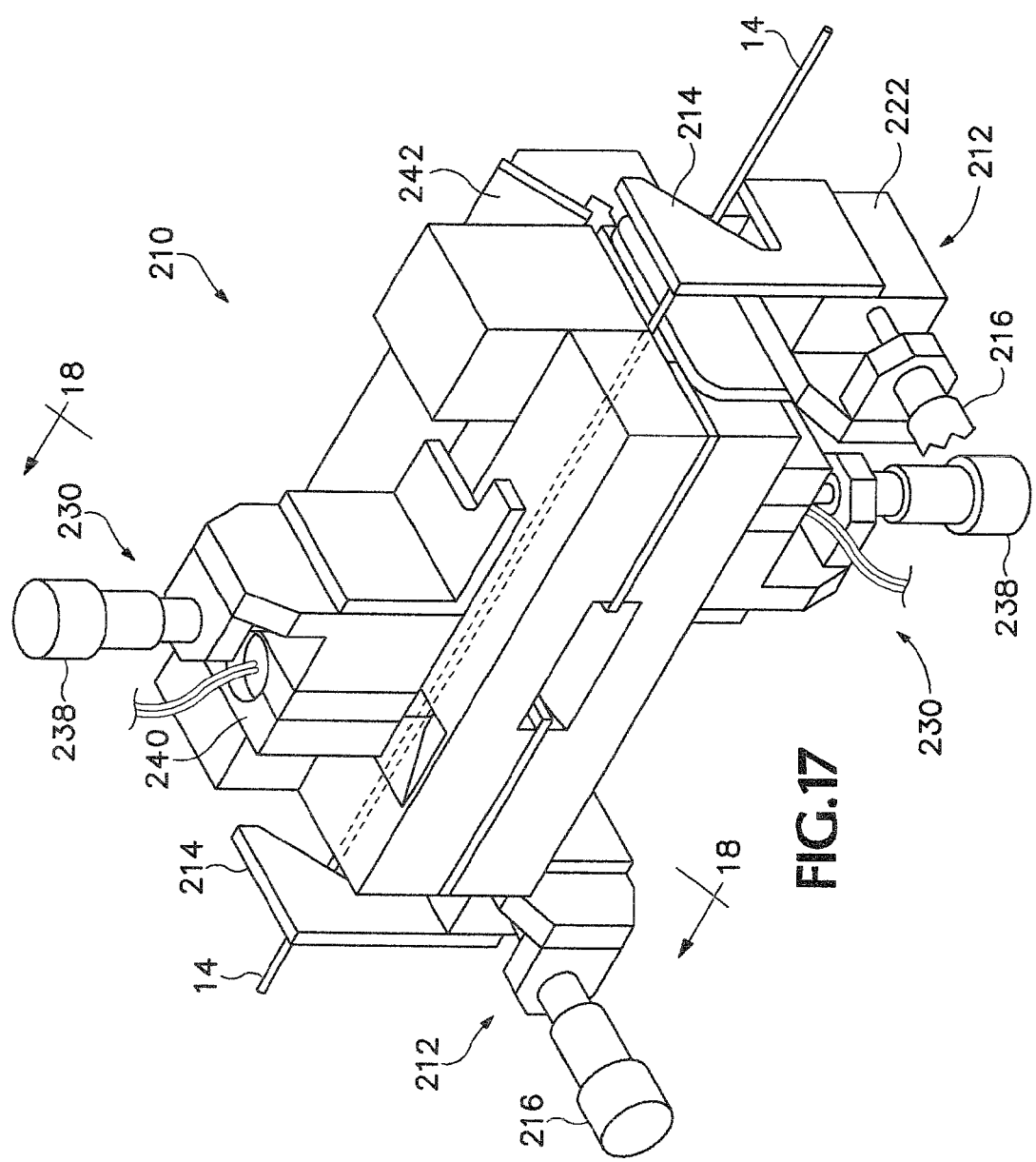
FIG. 17 is a perspective view of a reflow oven according to the present invention.
Figure 18:
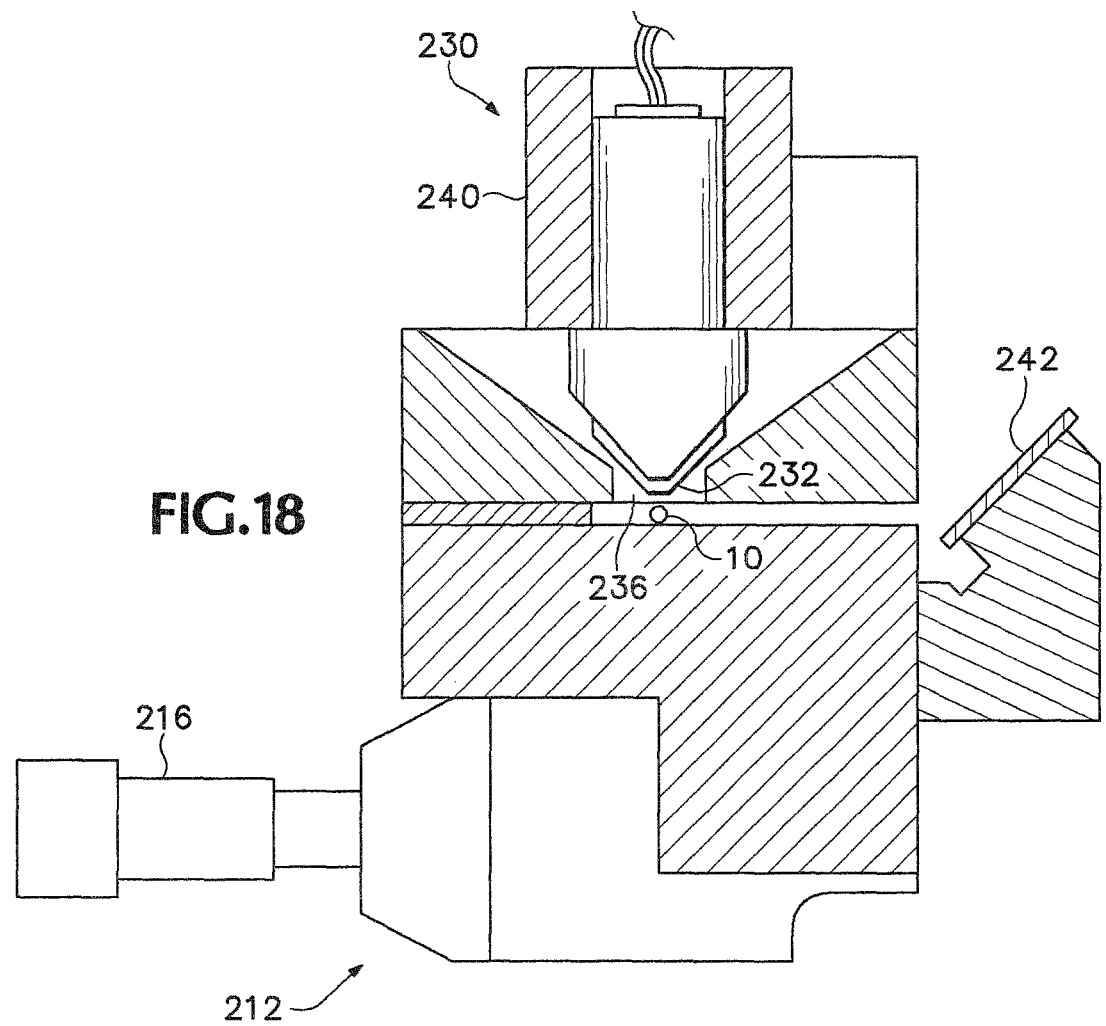
FIG. 18 is a sectional view of the reflow oven of FIG. 17 taken along line 18-18 of FIG. 17.

Referring to FIG. 16, the fusing of wires 14 about mandrel 12 is shown in schematic overview. FIGS. 17-18 show a physical representation of one embodiment of a reflow oven for accomplishing that task. The fusing process includes the progressive remelting of the insulation of wires 14 in reflow zones 200, 201, 202 and 203 (collectively forming a reflow oven 28). Each reflow zone remelts insulation 16 over a mutually distinct angular portion 17 (FIG. 5) of working material 10 so that wires 14 are held in place in the area of melted insulation, by the nearby unmelted insulation 16.

Among the critical adjustments that are made in the process is a speed adjustment 204 for the working material as it passes through the remelt zones, a working material centering adjustment 205, and an intensity and distance adjustment 206 for each radiant energy application device. A visual inspection system 207 aids an operator in adjusting the reflow oven 28 to achieve the best results.

Figure 19:
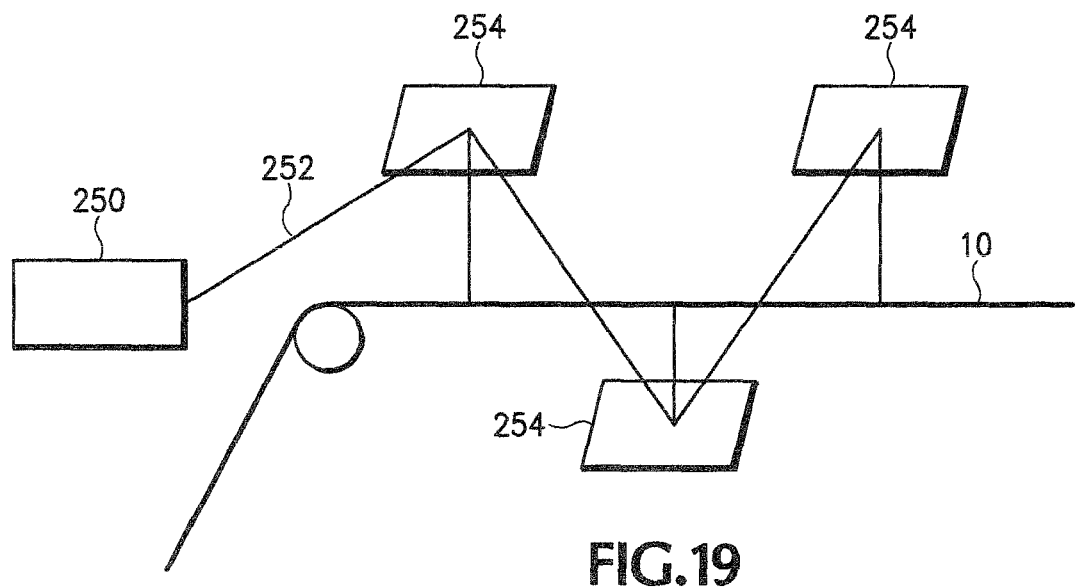
FIG. 19 is an illustration of an alternative preferred embodiment of the reflow process.

FIGS. 17-19 show a stage 210 of a reflow oven assembly 28 through which the working material 10 is passed in order to briefly melt the insulation about wires 14, sequentially in localized angular extents, to fuse insulated wires 14 together. Skilled persons will recognize that an additional stage or stages could be placed after stage 210, the first one rotated by 90.degree. Stage 210 includes two reflow zones, such as zones 200 and 201.

On either end of stage 210 is a wire guide assembly 212. Assembly 212 includes a 45.degree. guide plate 214, and a wire guide micrometer stage 216 that pushes on a slide block 222 that supports guide plate 214. By turning stage 216 guide plate 214 is moved, causing the working material 10 to be moved relative to stage 210. Two cartridge heater assemblies 230, each including a cartridge heater 232, and a heater micrometer stage 238, for moving block 240, which supports cartridge heater 232. By moving stage 238 heater 232 is moved closer to or further away from a small window 236 that permits heat to radiate to working material 10. In one embodiment a filament heater is used in place of cartridge heater 232, having a filament made of "Kanthol D" available from Duralite corporation and having a resistance per meter for the 0.254 mm diameter wire of 26.7 ohms. A mirror 242 permits inspection of the reflow process and may be used by itself or in conjunction with a video camera (not shown).

In an alternative preferred embodiment (FIG. 19), working material 10 is fused together by a laser 250. A laser beam 252 is split and reflected by a sequence of beam splitter/mirrors 254 to be reflected onto working material 10 at a number of places, thereby remelting the insulation 16 of material 10.

The terms and expressions that have been employed in the foregoing specification are used as terms of description and not of limitation. There is no intention, in the use of such terms and expressions, of excluding equivalents of the features shown and described or portions thereof, it being recognized that the scope of the invention is defined and limited only by the claims which follow. In particular, although the case of a four wire lead has been discussed, leads having some other number of insulated wires could be used, including but not limited to 8, 12, 16, 24 or 36. In this application the term "continuous" does not mean "continuous in time" but rather refers to a process that may be brought to completion without reloading the machinery involved. The term "fused" means "joined together as by melting."

What is claimed:

1. A method of fabricating an implantable stimulation lead for delivering electrical pulses to tissue of a patient using, in part, a wire wrapping device, the wire wrapping device comprising a plurality of payout carriers for letting out wire conductors to be wrapped about work material, the method comprising:
   advancing work material to be wrapped with the wire conductors;
   operating the plurality of payout carriers to let out the wire conductors;
   rotating the plurality of payout carriers relative to the work material to wrap the wire conductors about the work material;
   providing an amount of twist to each wire conductor as the wire conductors are let out of the payout carriers to compensate for twist caused by the wrapping of the wire conductors about the work material;
   forming a lead body using the wrapped conductors; and
   fabricating a plurality terminals on the lead body, wherein the plurality of terminals are electrically connected to the conductive wires.

2. The method of claim 1 wherein the work material comprises a mandrel.

3. The method of claim 1 wherein the work material comprises one or more previously formed stimulation lead layers.

4. The method of claim 1 wherein each of the wire conductors let out by the plurality of payout carriers are coated with insulative material.

5. The method of claim 1 further comprising:
   applying heat to fuse insulative material of the respective wire conductors together.

6. The method of claim 1 wherein the amount of applied twist is adjustable.

7. The method of claim 6 wherein the wire wrapping device comprises a display and one or more controls to permit a user to vary the amount of applied twist.

8. The method of claim 6 wherein the amount of applied twist is automatically adjusted in response to a selection of one or more lead characteristics.

9. The method of claim 8 wherein one of the lead characteristics is a wire wrapping pitch.

10. The method of claim 1 wherein the amount of applied twist is controlled by controlling an amount of rotation of each of the plurality of payout carriers relative to a rate at which the plurality of payout carriers let out the conductive wires.

11. The method of claim 1 wherein each payout carrier of the plurality of payout carriers comprises an electric motor control assembly, wherein the electric motor control assembly includes a dancer arm, adapted to engage the conductive wire let out by the respective payout carrier, the dancer arm being adapted to provide a wire tension measurement, the electric motor control assembly further being adapted to control an electric motor of the respective payout carrier in a manner responsive to said wire tension measurement.

12. A method of fabricating an implantable stimulation lead for delivering electrical pulses to tissue of a patient using, in part, a wire wrapping device, the wire wrapping device comprising a plurality of payout carriers for letting out wire conductors to be wrapped about work material, the method comprising:
   advancing work material to be wrapped with the wire conductors;
   operating the plurality of payout carriers to rotate a respective spool of each payout carrier in a first direction to let out the respective wire conductor and to rotate the spool in a second direction to impart an amount of twist to the respective wire conductor as the respective wire conductor is let out by the respective payout carrier;
   rotating the plurality of payout carriers relative to the work material to wrap the wire conductors about the work material, wherein the twist applied to each wire conductor by the plurality of payout carriers compensates for twist applied to the wire conductors as the wire conductors are wrapped about the work material;
   forming a lead body using the wrapped conductors; and
   fabricating a plurality of terminals on the lead body, wherein the plurality of terminals are electrically coupled to the conductive wires.

13. The method of claim 12 wherein the work material comprises a mandrel.

14. The method of claim 12 wherein the work material comprises one or more previously formed stimulation lead layers.

15. The method of claim 12 wherein each of the wire conductors let out by the plurality of payout carriers are coated with insulative material.

16. The method of claim 12 further comprising:
   applying heat to fuse insulative material of the respective wire conductors together.

17. The method of claim 12 wherein the amount of applied twist is adjustable.

18. The method of claim 17 wherein the wire wrapping device comprises a display and one or more controls to permit a user to vary the amount of applied twist.

19. The method of claim 17 wherein the amount of applied twist is automatically adjusted in response to a selection of one or more lead characteristics.

20. The method of claim 19 wherein one of the lead characteristics is a wire wrapping pitch.

21. The method of claim 12 wherein each payout carrier of the plurality of payout carriers comprises an electric motor control assembly, wherein the electric motor control assembly includes a dancer arm, adapted to engage the conductive wire let out by the respective payout carrier, the dancer arm being adapted to provide a wire tension measurement, the electric motor control assembly further being adapted to control an electric motor of the respective payout carrier in a manner responsive to said wire tension measurement.

* * * * *